(12) United States Patent
Lin et al.

(10) Patent No.: US 11,590,174 B2
(45) Date of Patent: Feb. 28, 2023

(54) METHOD FOR TREATING OSTEOARTHRITIS

(71) Applicant: E-DA CANCER HOSPITAL, Kaohsiung (TW)

(72) Inventors: Ming-Wei Lin, Kaohsiung (TW); Hsin-Yi Tsai, Kaohsiung (TW); I-Ming Jou, Kaohsiung (TW); Chin-Hsien Wu, Kaohsiung (TW)

(73) Assignee: E-DA CANCER HOSPITAL, Kaohsiung (TW)

( * ) Notice: Subject to any disclaimer, the term of this patent is extended or adjusted under 35 U.S.C. 154(b) by 178 days.

(21) Appl. No.: 17/035,697

(22) Filed: Sep. 29, 2020

(65) Prior Publication Data
US 2022/0096557 A1 Mar. 31, 2022

(51) Int. Cl.
| | | |
|---|---|---|
| *A61K 35/28* | (2015.01) | |
| *A61K 9/00* | (2006.01) | |
| *A61P 19/02* | (2006.01) | |
| *A61K 35/17* | (2015.01) | |
| *A61K 45/06* | (2006.01) | |

(52) U.S. Cl.
CPC ............ *A61K 35/28* (2013.01); *A61K 9/0019* (2013.01); *A61K 35/17* (2013.01); *A61K 45/06* (2013.01); *A61P 19/02* (2018.01)

(58) Field of Classification Search
None
See application file for complete search history.

(56) References Cited

U.S. PATENT DOCUMENTS

2002/0049176 A1* 4/2002 Anderson .......... C07K 14/4705 514/44 R
2021/0205358 A1* 7/2021 Elliott .................... A61K 47/26

OTHER PUBLICATIONS

Lee, A. et al. Mitochondrial Transplantation Ameliorates the Development and Progression of Osteoarthritis. Immune Network 22(2) 1-17, Apr. 2022. (Year: 2022).*

* cited by examiner

*Primary Examiner* — Ralph J Gitomer

(57) ABSTRACT

Disclosed herein is a method for treating an osteoarthritis in a subject in need thereof. The method mainly includes administering to the subject an effective amount of isolated mitochondria. According to some embodiments of the present disclosure, the isolated mitochondria are administered to the subject in need in the amount of about 1 mg/kg to about 100 mg/kg.

11 Claims, 8 Drawing Sheets

METHOD FOR TREATING OSTEOARTHRITIS

BACKGROUND OF THE INVENTION

1. Field of the Invention

The present disclosure relates to the field of disease treatment. More particularly, the disclosure invention relates to a method for treating osteoarthritis by use of isolated mitochondria.

2. Description of Related Art

Osteoarthritis (OA) is the most common form of arthritis, which affects about 15% of the population worldwide. It occurs when the protective cartilage that cushions the ends of bones wears down over time, which causes irreversible changes in the bone and deterioration of the connective tissues holding the joint together and attaching muscle to bone, so to causes inflammation of the joint lining. Such joint disease leads to chronic cartilage degradation that involves synovial inflammation, subchondral bone remodeling and the formation of osteophytes even in the early stages of the disease.

Many therapeutic medicaments have been development for treating OA, such as non-steroidal anti-inflammatory drugs (NSAIDs) used to reduce inflammation, and acetaminophen and duloxetine for relieving pain. Surgeries can be applied to severe conditions of OA, helping symptomatic patients maintain an ordinary life by replacing artificial joints or bones. However, none of said treatments can completely cure OA.

Recent studies showed that atrophy and weakness in quadriceps muscles and pro-inflammatory cytokines released by osteocytes affect pathological conditions and pain intensity of OA. The development and progression of OA is believed to be significantly related to reactive oxygen species (ROS) that are free radicals containing oxygen molecules, and oxidative stress. As both the predominant site for ROS production and the prime target of ROS molecules, it is believed that mitochondria play a key role in OA pathogenesis. Specifically, ROS causes mitochondrial respiratory chain inhibition, adenosine triphosphate (ATP) decrease, and mitochondrial DNA (mtDNA) mutation. It was also reported that oxidative stress causes synoviocyte apoptosis in vitro through mitochondrial injury. All of them are related to the severity of the inflammatory process as they enhance functional failure and cell death, thereby reducing the survival of OA synoviocytes. However, how and to what extend mitochondria are involved in OA still remain unknown.

In view of the foregoing, there exists in the related art a need of a novel treatment of osteoarthritis (OA).

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to a method for treating osteoarthritis in a subject in need thereof. The method comprises administering to the subject an effective amount of isolated mitochondria.

According to one embodiment of the present disclosure, the isolated mitochondria are administered to the subject in the amount of about 1 to 100 mg/kg; preferably, about 10 to 50 mg/kg; more preferably, about 15 to 45 mg/kg.

According to some embodiments of the present disclosure, the isolated mitochondria are administered to the subject once every 3 to 10 days. In one preferred embodiment, the isolated mitochondria are administered to the subject once every 7 days.

According to some embodiments of the present disclosure, the isolated mitochondria are isolated from germ cells, stem cells, somatic cells, or a combination thereof.

Examples of the germ cells suitable for use in the present disclosure include, but are not limited to, gametocytes, spermatocytes, and oocytes. Non-limiting examples of the stem cells suitable for use in the present disclosure include mesenchymal stem cells, adult stem cells, embryonic stem cells, bone marrow stem cells, neural stem cells, limbal stem cells, and tissue-derived stem cells. Exemplary somatic cells suitable for use in the present disclosure include, but are not limited to, muscle cells, hepatocytes, neurons, fibroblasts, epithelial cells, adipocytes, bone cells, white blood cells, lymphocytes, platelets, and mucosal cells. According to one working example, the isolated mitochondria are isolated from muscle cells.

According to certain embodiments of the present disclosure, the isolated mitochondria are administered to the subject via peripheral joint injection. In some working examples, the isolated mitochondria are administered to the subject via intra-articular injection.

Alternatively or in addition, the present method further comprises administering to the subject an anti-inflammatory drug and/or an analgesic drug.

According to certain embodiments of the present disclosure, the anti-inflammatory drug is acetylsalicylic acid, celecoxib, diclofenac diflunisal, etodolac, ibuprofen, indomethacin, ketoprofen, ketorolac, meloxicam, nabumetone, naproxen, oxaprozin, piroxicam, salsalate, sulindac, tolmetin, prednisone, cortisone, methylprednisolone, or a combination thereof.

According to certain embodiments of the present disclosure, the analgesic drug is paracetamol, nefopam, codeine, amitriptyline, gabapentin, morphine, oxycodone, pregabalin, tapentadol, hyoscine butylbromide, tramadol, or a combination thereof.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 2B, sirt1; FIG. 2C, HO-1; and FIG. 2D, iNOS. *, $p<0.05$; , $p<0.001$; *, $p<0.005$.

DESCRIPTION

Figure 1A:
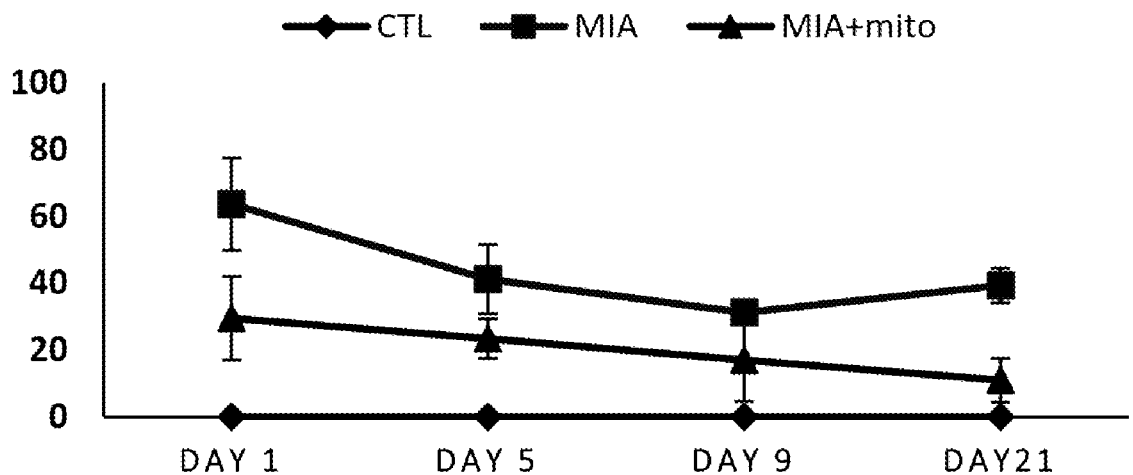
FIGS. 1A and 1B respectively depict the results of behavioral test of MIA-induced OA rats administered with specified treatments according to Example 1 of the present disclosure. CTL: control group; MIA: MIA-induced OA group; MIA+mito: MIA-induced OA rats treated with mitochondria. ***, $p<0.05$.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The term "isolated mitochondria" used herein refers to mitochondria separated from specific cells of eukaryotes by various known methods, for example, using a specific buffer solution or using a potential difference and a magnetic field to separate intact mitochondria from mammalian cells, while the biological mitochondrial activity is maintained.

The term "administering", "administered" or "administration" are used interchangeably herein to refer means administering isolated mitochondria for curing, preventing, ameliorating, and treating the symptoms of and/or reliving the pain associated with osteoarthritis, as described in the present disclosure to a subject in need.

The term "an effective amount" as used herein refers to the isolated mitochondria in an amount effective, at dosages, and for periods of time necessary, to provide a therapeutic benefit in the treatment of a condition or to delay or minimize one or more symptoms associated with the condition, so as to achieve the desired therapeutically desired result with respect to the treatment of osteoarthritis. An effective amount of the isolated mitochondria described herein means an amount of isolated mitochondria, alone or in combination with other therapeutic agents, which provides a therapeutic benefit in the treatment of the condition. In some working examples of the present disclosure, the amount of the isolated mitochondria is effective in stimulating the cell repair in synovial tissues in a subject with osteoarthritis.

The term "subject" or "patient" is used interchangeably herein and is intended to mean a mammal including the human species that is treatable by the method of the present disclosure. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated.

The term "peripheral joint" as used herein refers to the joints of the subject's body that defined as limb joints other than axis joints such as hips and shoulder joints. Peripheral joints include elbows, wrists, knees, and ankles.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery that isolated mitochondria are capable of down-regulating the expression of antioxidant proteins and inflammatory cytokines, delaying cell apoptosis and degradation, and stimulating cell repairing, therefor may be used to treat osteoarthritis. Accordingly, the present disclosure aims at providing a method of treating osteoarthritis by use of isolated mitochondria.

One aspect of the present disclosure is directed to a method for treating osteoarthritis in a subject in need thereof. The method comprises administering an effective amount of isolated mitochondria to the subject.

Mitochondria can be isolated from cells or tissues by any means known to those skilled persons in the art. Typical methods of isolating mitochondria are described, for example, in McCully et al., "Injection of isolated mitochondria during early reperfusion for cardioprotection," *Am J Physiol Heart Circ Physiol*, 296(1):H94-H105 (2009); Frezza et al., "Organelle isolation: functional mitochondria from mouse liver, muscle and cultured filroblasts," *Nature*

*protocols*, 2, 287-295 (2007); and a PCT publication entitled "Products and Methods to Isolate Mitochondria" (WO 2015192020); each of which is incorporated herein by reference. In general, tissue samples or cell samples are collected and then homogenized, and mitochondria are isolated by repetitive centrifugation. Alternatively or in addition, the cell homogenate is filtered through nylon mesh filters, which are commercially available in the form of a kit. In one working example, mitochondria are isolated from animal tissues with the aid of a mitochondria isolation kit. Optionally, the isolated mitochondria may be maintained in vitro by any means known to those skilled in the art. Generally, the mitochondria isolated from cells retain their intrinsic biological activity as they were in the cells.

Mitochondria suitable for use in the present method may be isolated from cells or tissues of an autogenous source, an allogeneic source, and/or a xenogeneic source. Autologous mitochondria are mitochondria obtained from tissues or cells of the same individual; allogeneic mitochondria are mitochondria obtained from tissues or cells of the same species but different individuals; and xenogeneic mitochondria refers to mitochondria obtained from individuals belonging to different species. Specifically, mitochondria may be isolated from somatic cells, germ cells, and/or stem cells within an individual, or within different individuals of one species, or among different individuals of different species. Exemplary germ cells include gametocytes, spermatocytes, or oocytes. Exemplary stem cells suitable for the present disclosure include mesenchymal stem cells, adult stem cells, embryonic stem cells, bone marrow stem cells, neural stem cells, limbal stem cells, and tissue-derived stem cells. Exemplary somatic cells suitable for the present disclosure include, but are not limited to, muscle cells, hepatocytes, neurons, fibroblasts, epithelial cells, adipocytes, bone cells, white blood cells, lymphocytes, platelets, and mucosal cells. According to some embodiments of the present application, mitochondria are isolated from muscle tissues and cells of a single rat. According to some embodiments of the present application, mitochondria are isolated from an autologous muscle tissues and/or cells of a rat. According to some embodiments of the present disclosure, mitochondria are isolated from muscle tissues and/or cells of an autologous source, e.g., human.

According to embodiments of the present disclosure, isolated mitochondria are administered to a subject having an arthritis disease, specifically osteoarthritis, in an amount sufficient to ameliorate symptoms associated therewith. According to some embodiments of the present disclosure, the isolated mitochondria are administered to the subject in the amount of about 1 mg/kg to about 100 mg/kg per body weight of the subject; for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, or 100 mg/kg. Preferably, the isolated mitochondria are administered to the subject in the amount of about 10 mg/kg to about 50 mg/kg, such as about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 mg/Kg. More preferably, the isolated mitochondria are administered to the subject in the amount of about 15 to 45 mg/kg, such as about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 mg/Kg. In one specific example of the present disclosure, the isolated mitochondria are administered to the subject having osteoarthritis in the amount of about 16 mg/kg. In an alternative example of the present disclosure, the isolated mitochondria are administered to the osteoarthritis subject in the amount of about 21 mg/kg. In another example of the present disclosure, the isolated mitochondria are administered to the osteoarthritis subject in the amount of about 32 mg/kg. In another example of the present disclosure, the isolated mitochondria are administered to the osteoarthritis subject in the amount of about 43 mg/kg. In addition, the isolated mitochondria are administered at a frequency of four times a day to once every three months. In some embodiments, the isolated mitochondria described herein are administered at a frequency of four times a day, three times a day, twice a day, once a day, once every other day, once every third day, once every week, once every other week, once monthly, once every other month, or once every three months. In some embodiments, the isolated mitochondria are administered to the subject at a frequency of once every three to ten days. Preferably, the isolated mitochondria are administered to the subject at a frequency of once every seven days.

The present isolated mitochondria can be administered by any route that may effectively transports the isolated mitochondria to the appropriate or desired site of action. In some embodiments, the isolated mitochondria are parenterally administered to an appropriate or a desired site. Exemplary suitable parenteral route includes, but is not limited to, peripheral joint, intravenous, intramuscular, intra-arterial, intramedullary, intrathecal, intraventricular, intradermal, subcutaneous, and intraperitoneal. Specifically, contemplated routes are intravenous administration (e.g., systemic intravenous injection), and/or regional administration to an affected site (i.e., direct administration to lesioned joints, e.g., peripheral joint injection). Suitable routes vary, as recognized by those skilled in the art, depending on the particular condition being treated, the severity of the condition, the individual patient parameters including age, physical condition, size, gender and weight, the duration of the treatment, the nature of concurrent therapy (if any), the dosage and the nature of active ingredients, genetic factors and like factors within the knowledge and expertise of the health practitioner. These factors are well known to those of ordinary skill in the art and can be addressed with no more than routine experimentation. In general, the most appropriate route of administration depends on a variety of factors including the agent's stability in the environment of the circulatory system, and/or the condition of the subject (e.g., whether the subject is able to tolerate intra-articular injection). According to some embodiments of the present disclosure, the isolated mitochondria are administered via peripheral joint injection. In some preferred embodiment, the isolated mitochondria are administered via intra-articular injection into knees.

Preferably, the isolated mitochondria are prepared as a composition suitable for injection at a target site (e.g., knee joints). According to some embodiment of the present disclosure, the isolated mitochondria are suspended in an aqueous solution to form an injection composition. Examples of aqueous solution suitable for the present method including, but are not limited to, distilled water, glucose solution, xylitol solution, D-mannitol solution, fructose solution, saline, dextran solution, amino acid solution, Ringer's solution, Ringer's lactate solution, phosphate buffer, and phosphate-buffered saline. According to some embodiments of the present disclosure, the isolated mitochondria are suspended in a saline solution. In one specific example of the present application, mitochondria isolated from muscle tissues are suspended in a solution of phosphate-buffered saline (PBS).

The isolated mitochondria, as described herein, can be administered in combination with one or more active ingredients or other pharmaceutical agents (e.g., therapeutically and/or prophylactically active agents) useful in treating, reducing the risk for, or delaying the onset of osteoarthritis as described herein. The isolated mitochondria and the additional pharmaceutical agents may be administered successively or simultaneously to the subject in need thereof. According to some optional embodiments, the present method further comprises administering to the subject pharmaceutical agents including an anti-inflammatory drug and an analgesic drug. The exemplary anti-inflammatory drug suitable for treating osteoarthritis comprises acetylsalicylic acid, celecoxib, diclofenac diflunisal, etodolac, ibuprofen, indomethacin, ketoprofen, ketorolac, meloxicam, nabumetone, naproxen, oxaprozin, piroxicam, salsalate, sulindac, tolmetin, prednisone, cortisone, and methylprednisolone. The exemplary analgesic drug suitable for treating osteoarthritis includes, but is not limited to, paracetamol, nefopam, codeine, amitriptyline, gabapentin, morphine, oxycodone, pregabalin, tapentadol, hyoscine butylbromide, and tramadol.

According to the present disclosure, the subject refers an animal that is treatable with and benefit from the methods of the present disclosure. Examples of the animal include, but are not limited to, a human, rat, mouse, guinea pig, monkey, pig, goat, cow, horse, dog, cat, bird and fowl. In one exemplary embodiment, the subject is a rat. In another exemplary embodiment, the subject is a human.

By the virtue of the above features, the present method can effectively reverse and reduce the oxidative stress and inflammation in injured tissues of subjects suffered from osteoarthritis. In addition, administration of intact mitochondria also stimulates cell repairing and prevents articular cartilage from wearing, such that the present method can effectively cure osteoarthritis.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Animal and Housing Conditions
Male Sprague Dawley (SD) rats (5 weeks old, weight about 151-200 g) were housed (3 rats per cage) in a room that was maintained at a 12/12-hr light/dark cycle at the temperature of 22±2° C. with access to food and water ad libitum. All behavioral studies were performed during the dark cycle.

Induction of Animal Model for Osteoarthritis (OA)
The SD rats were randomly assigned into three groups (n=6 for each group) as listed below:

Group 1: Sham treatment group (control group, CTL), in which 100 μl of 0.9% saline was intra-articularly injected to the right knee of pelvic limbs;

Group 2: Monosodium iodoacetate (MIA)-induced OA group (MIA), in which 100 μl of MIA was injected through the patellar ligament into the intra-articular space of the right knee of the pelvic limb, followed by PBS injection; and Group 3: Mitochondria treatment group (MIA+mito), in which XX volume of MIA was intra-articularly injected to the right knee of pelvic limbs of MIA-induced OA rats, followed by injection of isolated mitochondria (20 mg×2)

Isolation of Mitochondria
Mitochondria were isolated from the autogenous muscle tissues (200 mg of leg muscle tissues) of each rats in the present study with the aid of mitochondrial isolation kit. Mitochondrial viability was assessed by Mito TRACKER™ according to instructions provided by the manufacturer. 20 mg of mitochondria were separated from the muscle sample followed by suspending them in 1 mL of PBS.

Behavioral Assessment
Motor behavior was assessed via Combined Behavioral Score (CBS) reported by Gale et al., (see, "Spinal cord contusion in the rat: behavioral analysis of functional neurologic impairment", *Experimental Neurology*, vol. 88(1), 123-134, 1985) and Nakae et al., (see, "The animal model of spinal cord injury as an experimental pain model", *J Biomed Biotechnol* 2011:939023, 2011). Briefly, a CBS was developed to measure locomotor function in rats. In this study, following MIA-induced OA model establishment and mitochondria injection, CBS of each rats were recorded in accordance with the category of motor score, as summarized in Table 1.

TABLE 1

Motor score of CBS

| | General description of motor score | Points |
|---|---|---|
| 0 | Normal walking | 0 |
| 1 | Walks with mild deficit | 5 |
| 2 | Hindlimb can support weight | 15 |
| 3 | Frequent movement of hindlimb, no weight support | 25 |
| 4 | Minor movement in hindlimb, no weight bearing | 40 |
| 5 | No movement in hindlimb, no weight bearing | 45 |

Western Blot Analysis
Joint tissue samples were dissected from rats and then washed with PBS. Total protein of the tissue samples were extracted, and the concentrations of extracted protein were determined by use of protein assay kit. Equal quantities of total protein were separated by electrophoresis on 10% SDS-PAGE and transferred onto PVDF membranes. Membranes were blocked with 5% skimmed milk in TBST (tris-buffered saline (TBS) and 0.1% polysorbate (TWEEN® 20)) solution at 37° C. for 1 hour followed by washing the membranes with 1×TBST, then membranes were incubated with primary antibodies at 4° C. overnight. Membranes were developed using an ECL™ detection system subsequent to incubation with peroxidase-conjugated secondary antibodies at 37° C. for 1 hour.

Determination of Oxidative Stress Level
The homogenates of dissected tissues were centrifuged at 400×g at 4° C. for 30 minutes, then subjected to the measurement by using a 3-nitrotyrosine ELISA kit and to the lipid peroxidation (MDA) assay by using a MDA assay kit, so that reactive oxygen species (ROS) levels of the tested tissues were determined.

Determination of Cytokine Level
Nitrotyrosine, interleukin 6 (IL-6), interleukin 1β (IL-1β), tumor necrosis factor α (TNF-α), and matrix metallopeptidase (MMP13) levels were quantitatively measured using ELISA following the manufacturer's protocol. The protein concentrations were determined by using protein assay dyes.

Statistical Analysis

All results were presented as means±standard deviation. Statistical analysis was performed by one-way analysis of variance (ANOVA) for multiple comparisons, a statistically significant difference was indicated asp-value <0.05.

Tissues Sections

Wet joint tissues were sampled and trimmed from sacrificed rats, and dehydrated by serial alcohol solution, followed by soaking and fixing with 10% neutral formalin liquid. Next, the tissues were embedded by paraffin wax. The paraffin-embedded tissues were cut at a thickness of 3 if needed.

Digital Imaging

All glass slides were digitized with a digital slide scanner at ×40 (0.26 μm/pixel) with High precision (High precision autofocus). The thus-obtained whole-slide images were viewed with analytic software (e.g., DSAssistant and Easy-Scanner).

Example 1 Effect of Mitochondria Treatment on Behavioral Disability

In this example, SD rats were randomly assigned into three groups (n=6 for each group). On Day-0, rats in Group 1 were respectively treated with 100 μl of 0.9% saline via intra-articular injection into their knees, and rats in Group 2 and Group 3 were individually treated with 100 μl of monosodium iodoacetate (MIA, at a dose of 10 mg/kg) via intra-articular injection to induce osteoarthritis (OA) on their knees. Next, rats in Groups 1 and 2 were respectively treated with 1 mL of PBS solution, and those rats in Group 3 were independently treated with 20 mg of isolated mitochondria suspended in 1 mL PBS solution via knee joint injection once every week (i.e., on Day-7 and Day-14); total injection was 40 mg mitochondria per rat. Behavioral scores of each rat were recorded on Day-1, Day-5, Day-9 and Day-21 in accordance with the criterion listed in Table 1 above. After the 21st day, rats were sacrificed for further examination.

Figure 1B:
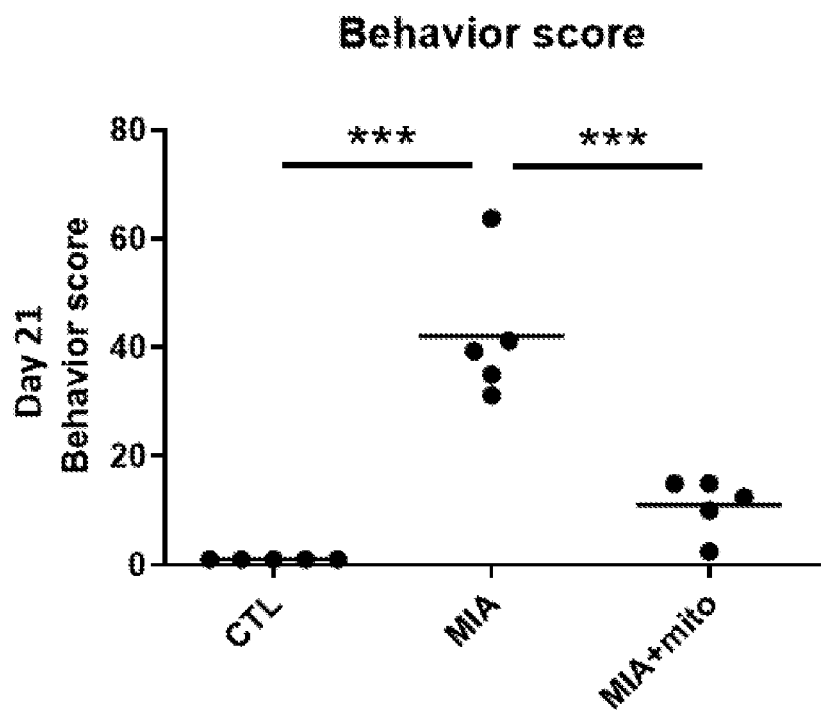

It was found that mitochondria injection gradually rescues the behavioral disability occurred in MIA-induced OA rats (FIG. 1A). Further, long term treatment (i.e., treatment for up to 21 days) of mitochondria significantly restored the locomotion activity of each MIA-induced OA rats as compared to that of the control group (FIG. 1B).

Example 2 Mitochondria Treatment Reduced Oxidative Stress and Inflammation in MIA-Induced OA Rats 2.1 Synovial Tissues Synovial tissues of control group and MIA-treated groups were dissected, and the expression of anti-oxidant proteins (i.e., nrf2 and sirt1) and inflammatory proteins (i.e., iNOS and HO-1) were examined via western blot. The quantitative results of each proteins were depicted in FIGS. 2A-2D.

Figure 2A:
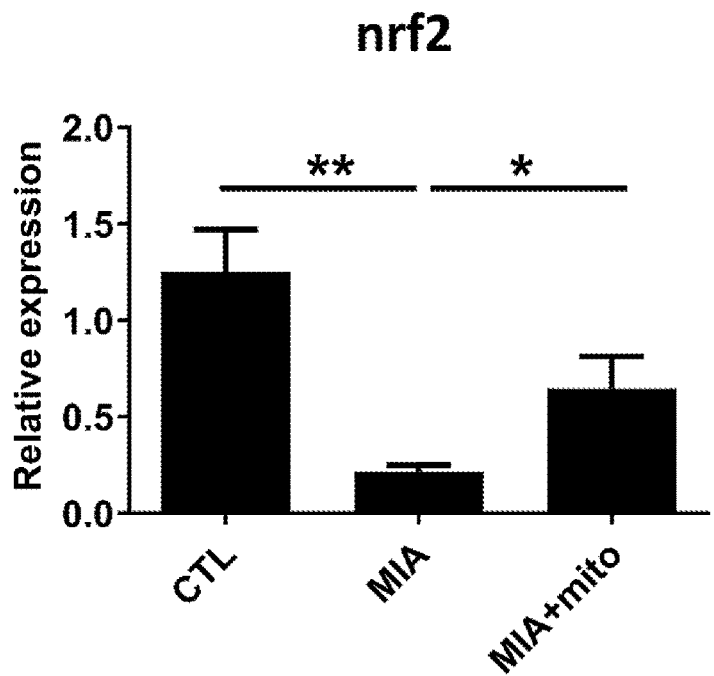
FIGS. 2A-2D respectively depicts the anti-oxidative ability in synovial tissues of MIA-induced OA rats administered with specified treatments according to Example 2 of the present disclosure. Two anti-oxidant proteins (i.e., nuclear factor erythroid 2-related factor 2 (nrf2) and NAD-dependent deacetylase sirtuin-1 (sirt1) and two inflammatory proteins (i.e., nitric oxide synthase (iNOS) and heme oxygenase-1 (HO-1)) from synovial tissues were examined, and the expression level thereof were respectively depicted in FIG. 2A, nrf2.
Figure 2B:
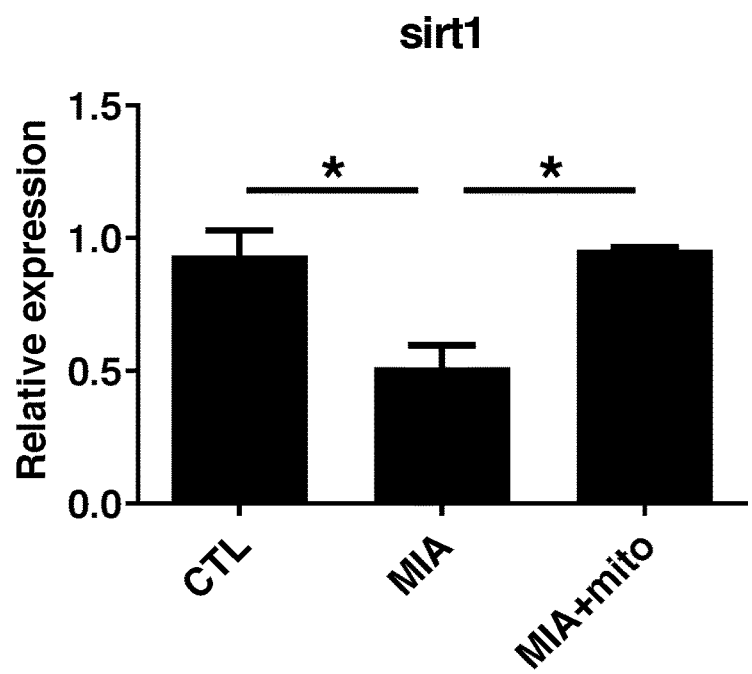
Figure 2C:
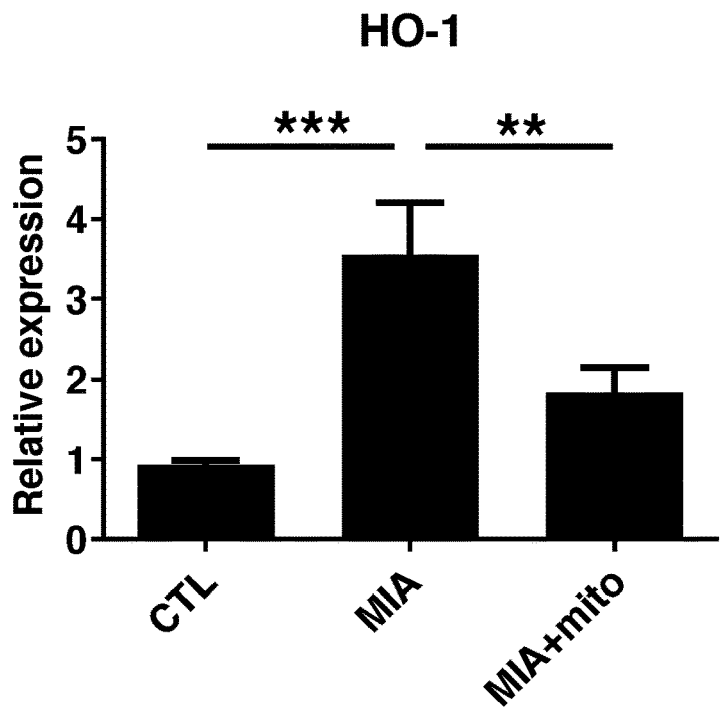
Figure 2D:
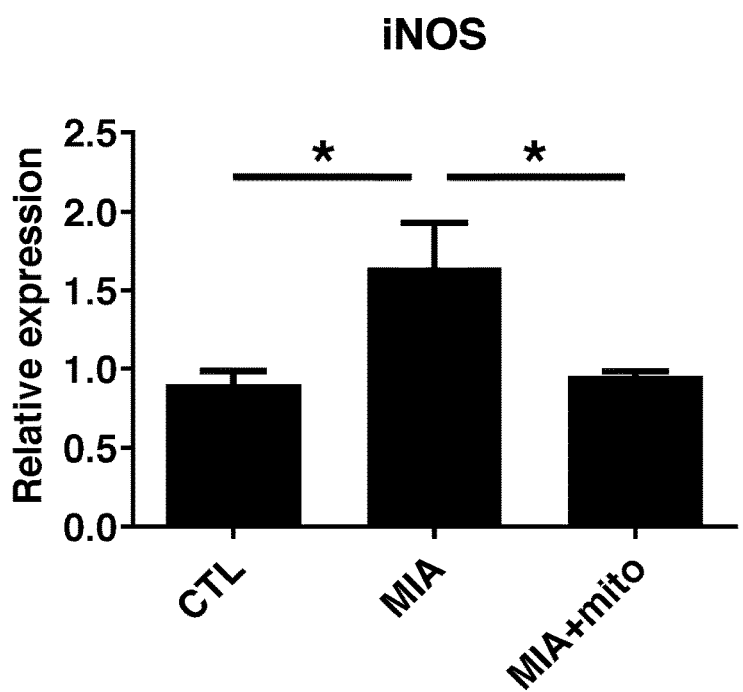

As depicted in FIGS. 2A and 2B, the administration of mitochondria significantly increased the expression of nrf2 and sirt1 proteins, as compared to those of the control group (i.e., MIA-induced OA rats treated with PBS). The data of FIGS. 2A and 2B indicated that the administration of intact mitochondria enhanced cellular regeneration in knee joints. In addition, the data of FIG. 2C and FIG. 2D indicated that the treatment of mitochondria reduced the oxidative stress and inflammation in MIA-induced OA rats.

2.2 Muscle Tissues

Figure 3:
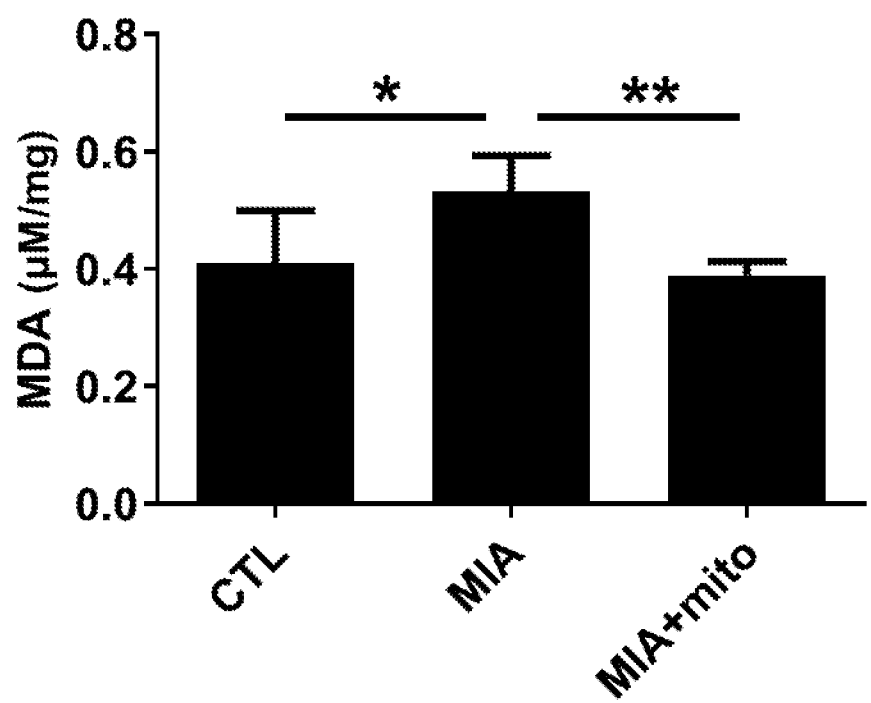
FIG. 3 depicts the expression level of malondialdehyde (MDA) in muscle tissues obtained from three groups of rats according to Example 2 of the present disclosure. *, $p<0.05$; **, $p<0.001$.

Muscle tissues of control group and MIA-treated groups were dissected, and the level of malondialdehyde (MDA) were tested by MDA assay to verify the oxidative stress in muscle tissues. The quantitative result of MDA level was depicted in FIG. 3, which demonstrated that administration of mitochondria significantly reduced the expression level of MDA, an oxidative stress indicator in muscles. The data of FIG. 3 suggested that oxidative stress of the injured tissue can be reversed by the administration of mitochondria.

2.3 Sera

Figure 4A:
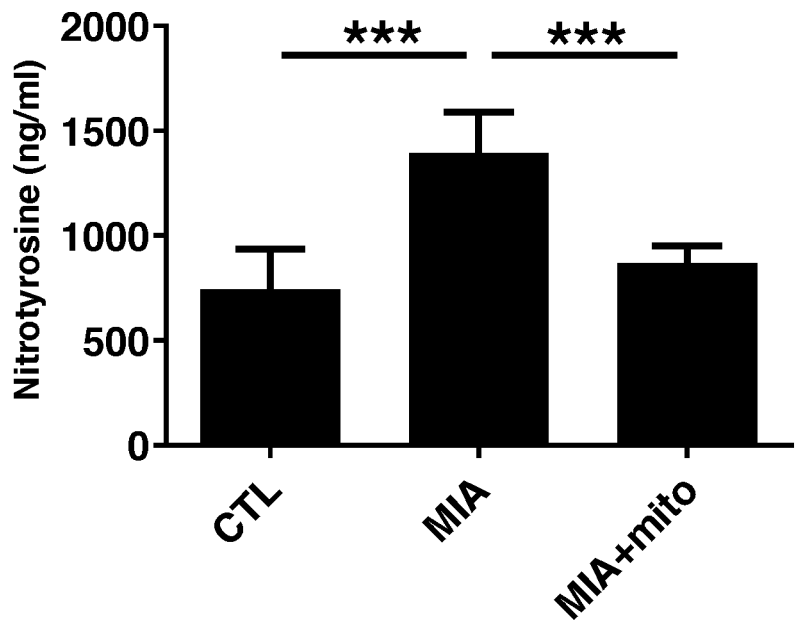
FIGS. 4A to 4E respectively depicts the expression level of anti-inflammatory factors in serum of three groups of rats according to Example 2 of the present disclosure. The expression levels of nitrotyrosine in three groups of rats were depicted in FIG. 4A; and the expression levels of IL-1β, IL-6, TNF-α, and MMP13 were depicted in FIGS. 4B to 4E, respectively. *, $p<0.05$; , $p<0.001$; *, $p<0.005$.
Figure 4B:
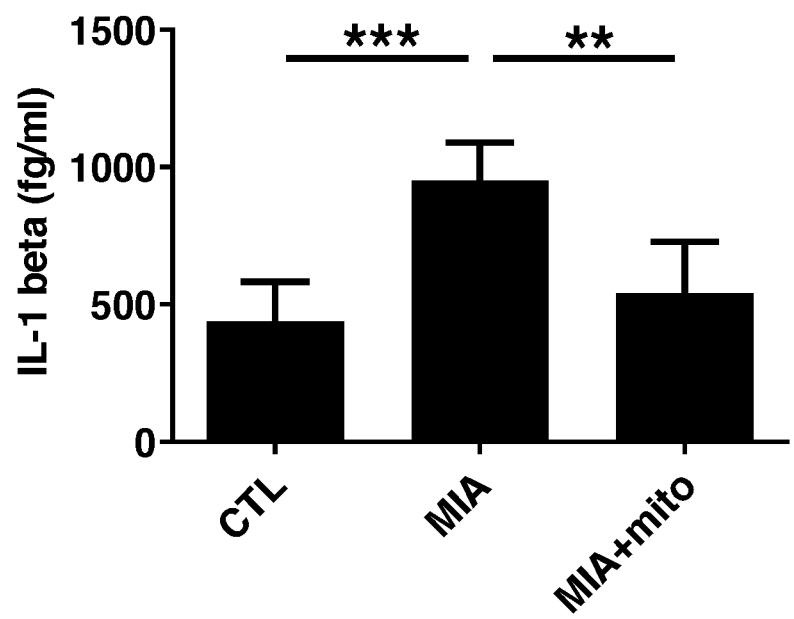
Figure 4C:
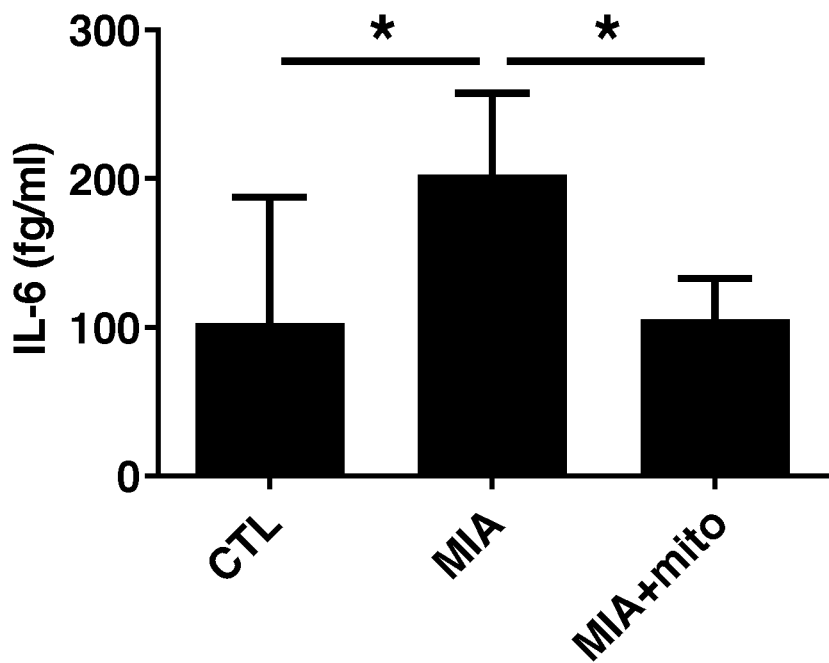
Figure 4D:
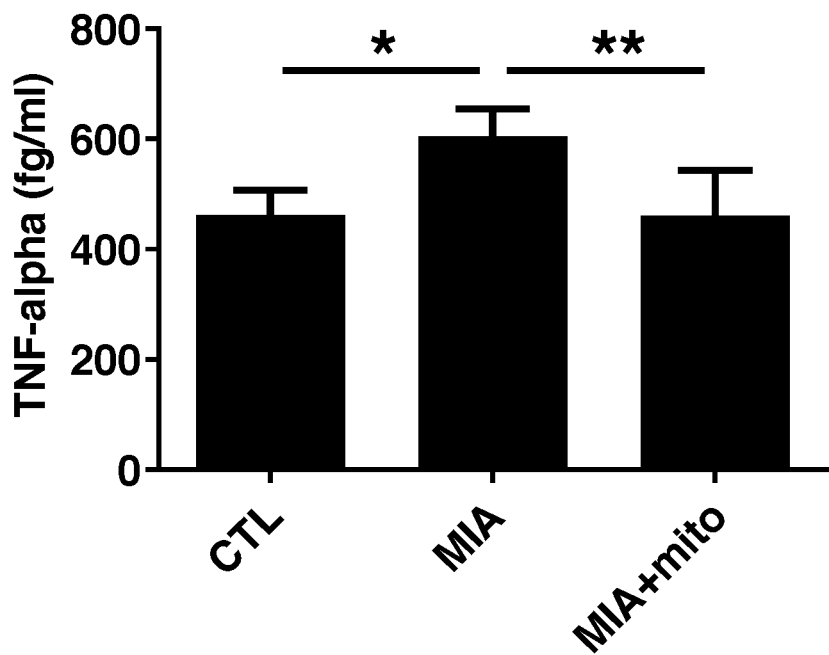
Figure 4E:
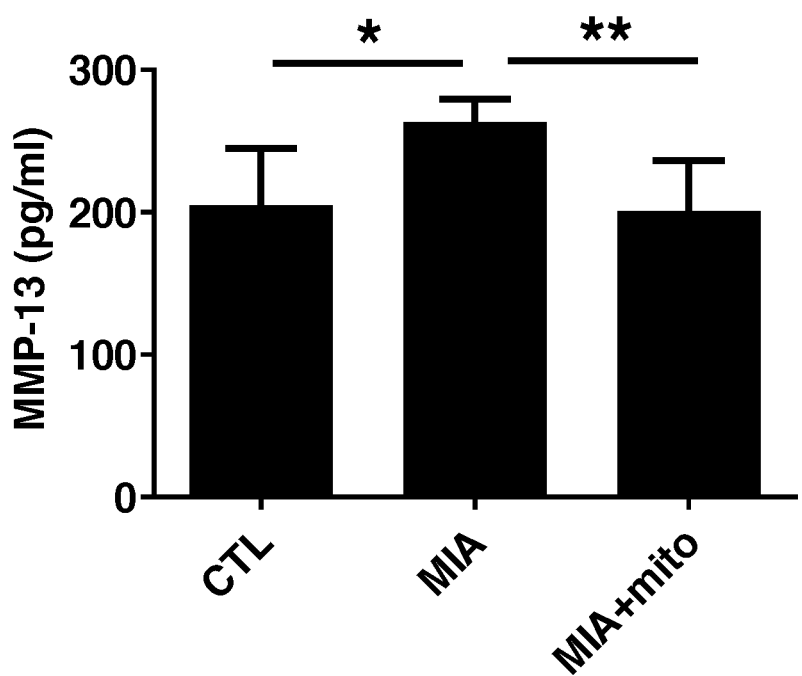

Sera of experimental rats were obtained, and the oxidative stress in mitochondria-treated and control (i.e., un-treated with mitochondria) rats were examined. Expression levels of nitrotyrosine (an oxidative stress indicator) and cytokines (including IL-1β, IL-6, TNF-α, and MMP13) were quantitatively measured by ELISA. Compared to the control group, the OA rats subjected to mitochondria treatment had a reduced nitrotyrosine level (see FIG. 4A); in addition, and a reduced cytokine levels in IL-1β, IL-6, TNF-α, and MMP13, respectively, indicating that the injected mitochondria may effectively reduce the inflammatory response in rats (FIGS. 4B-4E).

Figure 5:
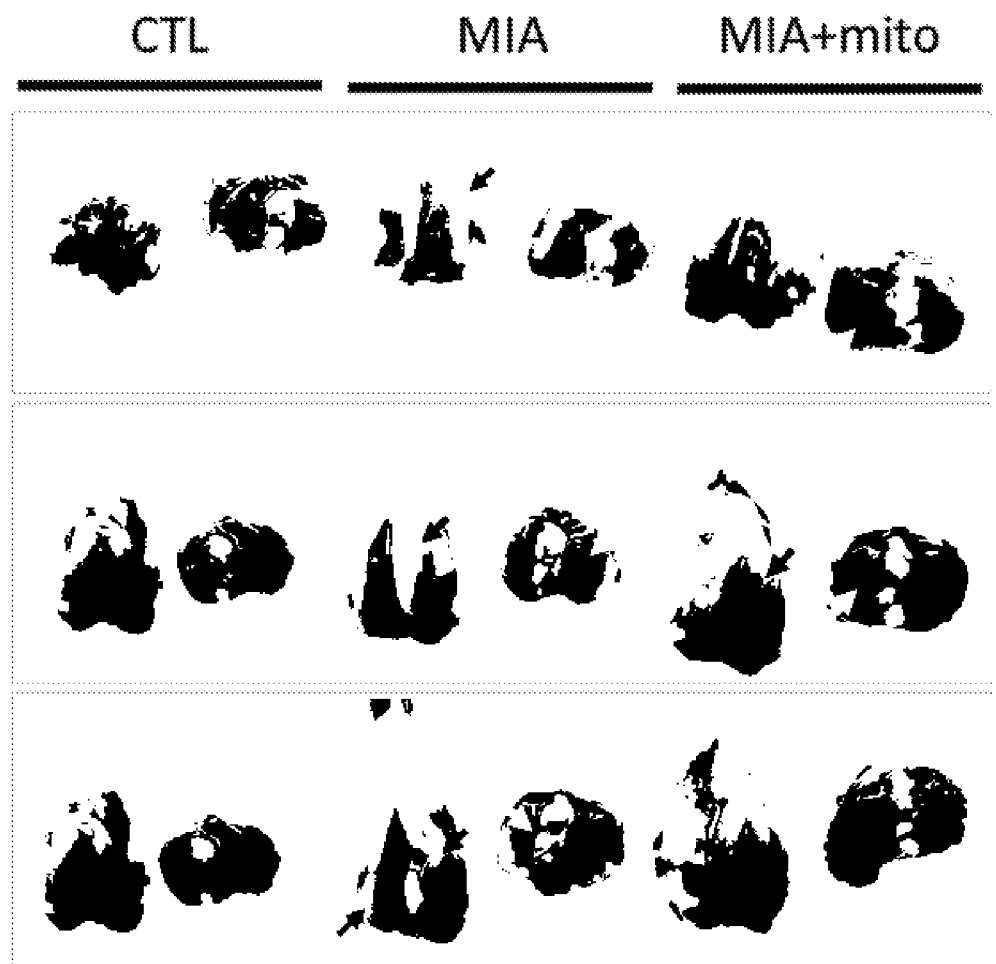
FIG. 5 is the photo taken from the dissected knee joints obtained from rats of three groups. Yellow arrow, cartilage wear; black arrow, cartilage deformation.

Example 3 Mitochondria Treatment Stimulated Tissue/Cell Regeneration in MIA-Induced OA Rats Three rats for each group were randomly picked out and sacrificed. The knee joints of all rats were dissected and fixed, and the appearance of dissected knee joints were examined via naked-eyes and optional with the aid of magnifying devices, followed by photographing via a digital camera. As shown in FIG. 5, in OA rats, the cartilages of knee joints were severely worn (yellow arrows in FIG. 5) and deformed (black arrows), while in the mitochondria-treated rats, the cartilages of joints were slightly worn, with only a few deformations.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating osteoarthritis in a subject in need thereof, comprising administering to the subject an effective amount of isolated mitochondria, which are isolated from muscle cells of the subject.

2. The method of claim 1, wherein the isolated mitochondria are administered to the subject in the amount of about 1-100 mg/kg.

3. The method of claim 2, wherein the isolated mitochondria are administered to the subject in the amount of about 10-50 mg/kg.

4. The method of claim 3, wherein the isolated mitochondria are administered to the subject in the amount of about 15-45 mg/kg.

5. The method of claim 1, wherein the isolated mitochondria are administered to the subject once every 3 to 10 days.

6. The method of claim 5, wherein the isolated mitochondria are administered to the subject once every 7 days.

7. The method of claim 1, wherein the isolated mitochondria are administered to the subject via peripheral joint injection.

8. The method of claim 7, wherein the isolated mitochondria are administered to the subject via intra-articular injection.

9. The method of claim 1, further comprising administering to the subject an anti-inflammatory drug and/or an analgesic drug.

10. The method of claim 9, wherein the anti-inflammatory drug is selected from the group consisting of acetylsalicylic acid, celecoxib, diclofenac diflunisal, etodolac, ibuprofen, indomethacin, ketoprofen, ketorolac, meloxicam, nabumetone, naproxen, oxaprozin, piroxicam, salsalate, sulindac, tolmetin, prednisone, cortisone, methylprednisolone, and a combination thereof.

11. The method of claim 9, wherein the analgesic drug is selected from the group consisting of paracetamol, nefopam, codeine, amitriptyline, gabapentin, morphine, oxycodone, pregabalin, tapentadol, hyoscine butylbromide, tramadol, and a combination thereof.

\* \* \* \* \*